(12) United States Patent
Carrillo, Jr. et al.

(10) Patent No.: US 8,715,165 B2
(45) Date of Patent: *May 6, 2014

(54) FLUID SEAL FOR ENDOSCOPE

(75) Inventors: Oscar R. Carrillo, Jr., Attleboro, MA (US); John C. Holmes, Chepachete, RI (US); Kevin Richardson, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 442 days.

This patent is subject to a terminal disclaimer.

(21) Appl. No.: 12/427,438

(22) Filed: Apr. 21, 2009

(65) Prior Publication Data

US 2009/0203960 A1 Aug. 13, 2009

Related U.S. Application Data

(63) Continuation of application No. 11/040,019, filed on Jan. 19, 2005, now Pat. No. 7,537,583, which is a continuation of application No. 10/447,440, filed on May 28, 2003, now Pat. No. 6,863,661, which is a continuation of application No. 09/573,035, filed on May 17, 2000, now Pat. No. 6,663,598.

(51) Int. Cl.
*A61B 1/00* (2006.01)
*A61B 1/12* (2006.01)
*A61M 39/00* (2006.01)

(52) U.S. Cl.
USPC ........... 600/104; 600/153; 600/154; 600/159; 604/167.01; 604/167.02; 604/167.03; 604/167.04; 604/533

(58) Field of Classification Search
USPC ........................ 600/104, 154, 159, 153, 156; 604/167.01–167.04
See application file for complete search history.

(56) References Cited

U.S. PATENT DOCUMENTS

| | | | | |
|---|---|---|---|---|
| 3,581,570 A | * | 6/1971 | Wortz | 600/549 |
| 4,128,918 A | * | 12/1978 | Wenk | 24/16 R |
| 4,198,958 A | | 4/1980 | Utsugi | |
| 4,240,411 A | * | 12/1980 | Hosono | 600/154 |
| 4,367,905 A | | 1/1983 | Nauta | |
| 4,653,477 A | | 3/1987 | Akui et al. | |
| 4,715,360 A | | 12/1987 | Akui et al. | |

(Continued)

FOREIGN PATENT DOCUMENTS

| | | |
|---|---|---|
| DE | 199 11 911 A1 | 9/1999 |
| DE | 199 16 866 A1 | 10/1999 |
| JP | 3-126428 A | 5/1991 |
| JP | 9-94253 A | 4/1997 |

*Primary Examiner* — John P Leubecker
*Assistant Examiner* — Arnaldo Torres Diaz
(74) *Attorney, Agent, or Firm* — Seager, Tufte & Wickem, LLC

(57) ABSTRACT

A seal is provided for effectively inhibiting the egress of fluids from the working channel of an endoscope when an elongate device having a region with a non-circular cross-sectional shape is disposed therein. The seal has a body portion with a proximal end adapted for insertion of the elongate device, a distal end adapted for connection to the proximal end of the endoscope, and a wall defining a lumen adapted to receive the elongate device and to provide access to the working channel of the endoscope. The seal includes a sealing element for sealing the region of the elongate device with a non-circular cross-sectional shape. The sealing element conforms to the profile of the non-circular region.

8 Claims, 5 Drawing Sheets

(56) References Cited

U.S. PATENT DOCUMENTS

| | | | |
|---|---|---|---|
| 4,740,195 A * | 4/1988 | Lanciano | 604/533 |
| 4,809,679 A * | 3/1989 | Shimonaka et al. | 600/154 |
| 4,920,953 A | 5/1990 | McGown | |
| 5,098,064 A | 3/1992 | Daly et al. | |
| 5,106,054 A | 4/1992 | Mollenauer et al. | |
| 5,127,626 A | 7/1992 | Hilal et al. | |
| 5,167,636 A | 12/1992 | Clement | |
| 5,199,948 A | 4/1993 | McPhee | |
| 5,242,389 A | 9/1993 | Schrader et al. | |
| 5,265,622 A * | 11/1993 | Barbere | 600/585 |
| 5,300,035 A * | 4/1994 | Clement | 604/167.01 |
| 5,304,143 A | 4/1994 | Green et al. | |
| 5,320,602 A | 6/1994 | Karpiel | |
| 5,338,313 A | 8/1994 | Mollenauer et al. | |
| 5,354,280 A | 10/1994 | Haber et al. | |
| 5,357,978 A | 10/1994 | Turk | |
| 5,385,552 A | 1/1995 | Haber et al. | |
| 5,391,153 A | 2/1995 | Haber et al. | |
| 5,395,342 A | 3/1995 | Yoon | |
| 5,397,302 A | 3/1995 | Weaver et al. | |
| 5,397,335 A | 3/1995 | Gresl et al. | |
| 5,407,433 A | 4/1995 | Loomas | |
| 5,441,486 A | 8/1995 | Yoon | |
| 5,456,284 A * | 10/1995 | Ryan et al. | 137/522 |
| 5,820,600 A | 10/1998 | Carlson et al. | |
| 5,823,995 A | 10/1998 | Fitzmaurice et al. | |
| 5,891,056 A | 4/1999 | Ramzipoor | |
| 5,919,004 A | 7/1999 | Christenson | |
| 5,921,971 A * | 7/1999 | Agro et al. | 604/523 |
| 5,997,515 A | 12/1999 | de la Torre et al. | |
| 6,053,861 A * | 4/2000 | Grossi | 600/154 |
| RE36,702 E | 5/2000 | Green et al. | |
| 6,200,262 B1 | 3/2001 | Ouchi | |
| 6,254,529 B1 | 7/2001 | Ouchi | |
| 6,663,598 B1 * | 12/2003 | Carrillo et al. | 604/167.01 |
| 6,863,661 B2 * | 3/2005 | Carrillo et al. | 604/167.01 |
| 7,537,583 B2 * | 5/2009 | Carrillo et al. | 604/167.01 |
| 7,645,266 B2 * | 1/2010 | Carrillo et al. | 604/167.01 |
| 2006/0142734 A1 | 6/2006 | Carrillo, Jr. et al. | |

* cited by examiner

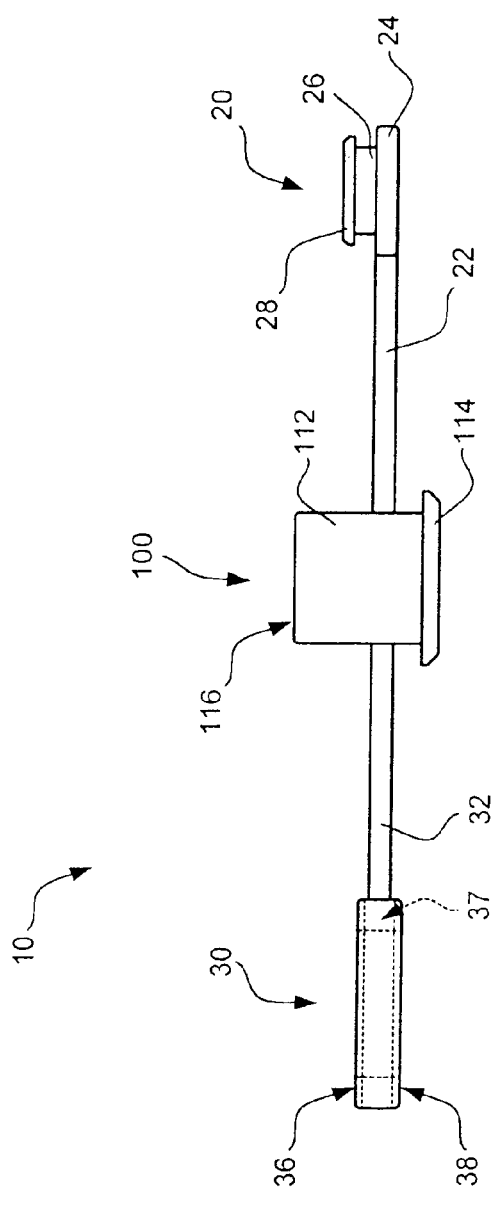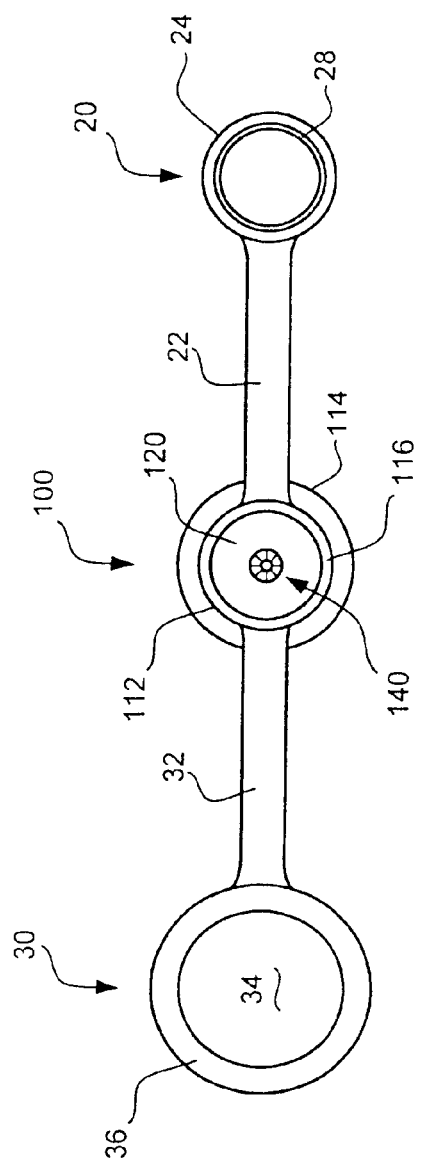
FIG. 1A
FIG. 1B

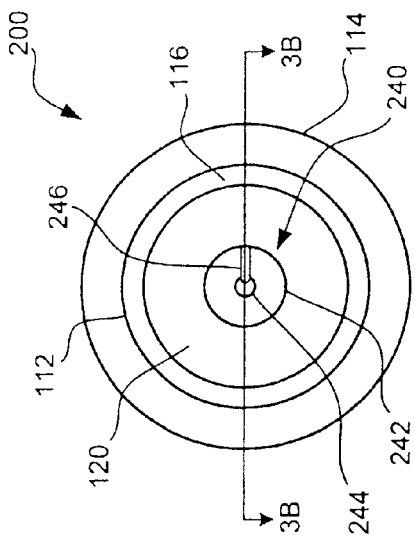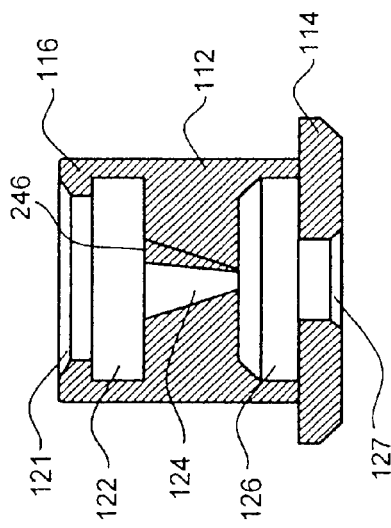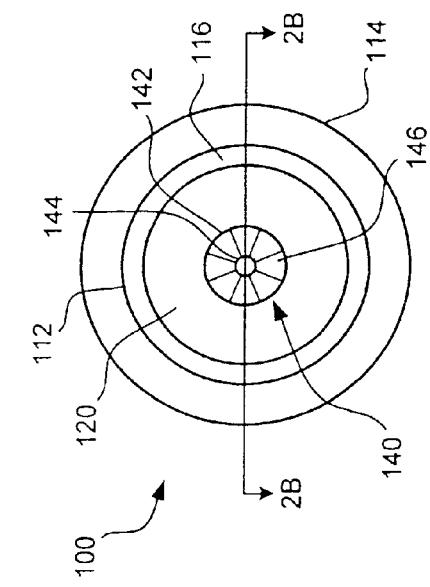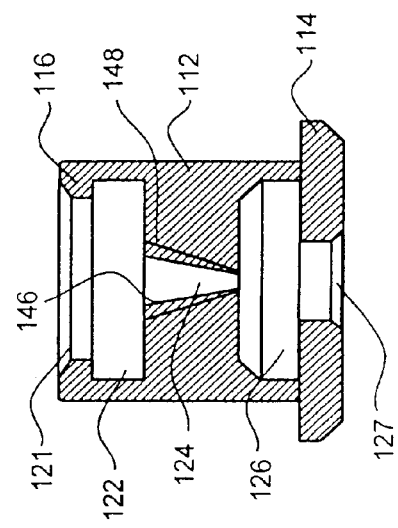

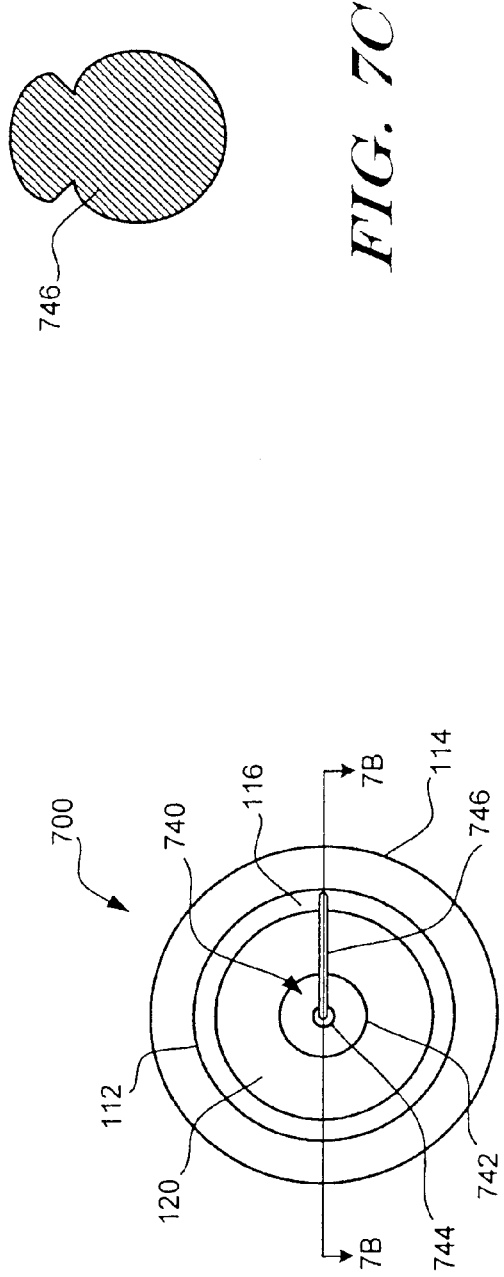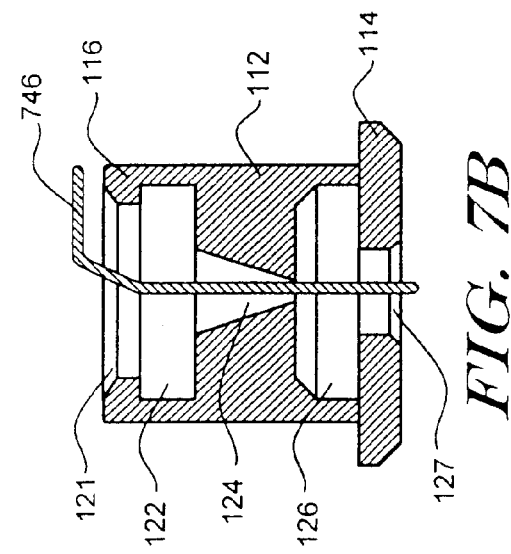

FLUID SEAL FOR ENDOSCOPE

CROSS-REFERENCE TO RELATED APPLICATIONS

This application is a continuation of U.S. application Ser. No. 11/040,019, filed Jan. 19, 2005, now U.S. Pat. No. 7,537,583; which is a continuation of U.S. application Ser. No. 10/447,440, filed May 28, 2003, now U.S. Pat. No. 6,863,661; which is a continuation of U.S. application Ser. No. 09/573,035, filed May 17, 2000, now U.S. Pat. No. 6,663,598; the entire disclosures of which are all incorporated herein by reference.

This application is related to U.S. application Ser. No. 11/361,605, filed Feb. 24, 2006, the entire disclosure of which is incorporated herein by reference.

FIELD OF THE INVENTION

The present invention general relates to endoscopic systems and procedures. More specifically, the present invention relates to seals for use in combination with an endoscope, sometimes referred to as endoscope seals or biopsy seals.

BACKGROUND OF THE INVENTION

Endoscopic procedures for treating abnormal pathologies within the alimentary canal system and biliary tree (including the biliary, hepatic, and pancreatic ducts) are increasing in number. The endoscope provides access to the general area of a desired duct using direct visualization. However, the duct itself must be navigated using a catheter in conjunction with a guidewire under fluoroscopy. A wide variety of catheters are known for treatment of such targeted anatomical regions. Examples of biliary catheters are disclosed in U.S. Pat. No. 5,397,302 to Weaver et al., U.S. Pat. No. 5,320,602 to Karpiel and U.S. Pat. No. 5,921,971 to Agro et al., the disclosures of which are hereby incorporated by reference.

Agro et al. '971 discloses a catheter for use in biliary procedures, wherein the catheter includes a shaft having a proximal end and a distal end. A guidewire lumen extends through the shaft from a proximal guidewire port located proximal of the distal end of the shaft, to a distal guidewire port located at the distal end of the shaft. The shaft may also include a slot or channel extending from a proximal end of the shaft to the proximal guidewire port. By utilizing a slot or channel, the proximal shaft portion has a non-circular profile or cross-section as best seen in FIGS. 5A and 6A of Agro et al. '971. Catheters incorporating such a guidewire opening and channel are often referred to as rapid exchange or single operator exchange type biliary catheters. One drawback with such rapid exchange or single operator exchange biliary catheters is the inability or relative difficulty in sealing around the non-circular shaft, such that fluid (bile liquid and air) may leak out of the working channel of the endoscope around the non-circular shaft of the biliary catheter.

Conventional endoscope seals are adapted to seal about catheters having circular shafts, and generally do not effectively seal about catheters having non-circular shafts. Such conventional seals are commercially available from Olympus, Fuji and Pentax. An example of a prior art endoscope seal is disclosed in U.S. Pat. No. 4,920,953 to McGown. The endoscope seals commercially available and the endoscope seal disclosed in McGown '953 generally include a body portion having a proximal end adapted to receive an elongate device such as a biliary catheter, a distal end adapted for connection to the proximal end of the endoscope, a lumen extending through the body portion, and a membrane disposed in the lumen, wherein the membrane includes a small circular hole or aperture. The circular aperture is sized to closely fit the elongate device inserted therein such that fluids (bile and air) do not readily escape from the working channel of the endoscope.

However, it can be readily appreciated that when a biliary catheter or other elongate device having a shaft with a non-circular cross section is placed through the circular aperture, at least a portion of the aperture does not engage the non-circular shaft. Accordingly, such prior art endoscope seals do not effectively inhibit the egress of bile liquids and air exiting the working channel of the endoscope when an elongate device having a non-circular cross-section is utilized. Because rapid exchange catheters are becoming more prevalent, and because such rapid exchange catheters have a non-circular shaft cross-section, there is a significant demand for an endoscope seal that effectively seals or inhibits the egress of fluid from the working channel of an endoscope, when a device having a non-circular shaft cross-section is used therewith.

SUMMARY OF THE INVENTION

The present invention satisfies this demand by providing an endoscope seal that effectively inhibits the egress of fluid from the working channel of an endoscope when an elongate device, such as a rapid exchange biliary catheter, having a non-circular shaft is disposed therein. The seal of the present invention is also suitable for other catheters having non-circular shafts such as rapid exchange vascular catheters. In addition, some embodiments of the present invention are perfectly suitable for sealing about elongate devices having shafts with a circular profile. Accordingly, the endoscope seals of the present invention are both versatile and functional, because they effectively inhibit, or at least reduce, the egress of fluids (bile and air) from the working channel of the endoscope when an elongate device having a circular or non-circular shaft is utilized.

The endoscope seals of the present invention include a body portion having a proximal end adapted for insertion of an elongate device such as a rapid exchange type catheter, a distal end adapted for connection to the proximal end of an endoscope, a lumen extending therethrough which is adapted to receive the elongate device and to provide access to the working channel of the endoscope, and a means for conforming to the non-circular shaft of the elongate device to inhibit the flow of fluid from the working channel of the endoscope.

In a first embodiment, the conforming means may comprise a protrusion extending radially inward in the lumen of the body portion. The protrusion may comprise a geometry that mates with the non-circular shaft of the elongate device. In a second embodiment, the conforming means may comprise a plurality of protrusions extending radially inward in the lumen body portion. The plurality of protrusions may be uniformly spaced about the circumference of the lumen and may have sufficient flexibility to conform to a non-circular geometry. In a third embodiment, the conforming means may comprise a sealing material such as a surgical foam that is disposed in the lumen of the body portion or injected therein just prior to use. In a fourth embodiment, the conforming means may comprise a sealing mandrel that it is disposed in the lumen of the body portion. The sealing mandrel conforms to the non-circular geometry to define a collective circular geometry that is readily sealed by a conventional circular aperture in the body portion. Whether a single protrusion, a plurality of protrusions, a sealing material or a sealing mandrel, the present invention provides endoscope seals that readily seal about an elongate devices having either circular or non-circular profiles.

The present invention also provides a variable diameter main body portion and a compression mechanism. The variable diameter main body portion may incorporate a conventional membrane with a circular aperture or may incorporate any of the conforming means described above. The compression mechanism may be used to tighten the variable diameter body portion to compress the membrane therein around a non-circular shaft to establish a fluid seal.

BRIEF DESCRIPTION OF THE DRAWINGS

FIG. 1A is a side view of the endoscope seal of the present invention;

FIG. 1B is a top view of the endoscope seal shown in FIG. 1A;

FIG. 2A is a top view of a body portion of an endoscope seal utilizing a plurality of protrusions;

FIG. 2B is a cross-sectional view taken along line 2B-2B in FIG. 2A;

FIG. 3A is a top view of a body portion of an endoscope seal utilizing a single protrusion;

FIG. 3B is a cross-sectional view taken along line 3B-3B in FIG. 3A;

FIG. 7A is a top view of a body portion of an endoscope seal utilizing a sealing mandrel;

FIG. 7B is a cross-sectional view taken along line 7B-7B in FIG. 7A; and

FIG. 7C is a cross-sectional view of the sealing mandrel illustrated in FIGS. 7A and 7B.

DETAILED DESCRIPTION OF THE PREFERRED EMBODIMENTS

Figure 4A:
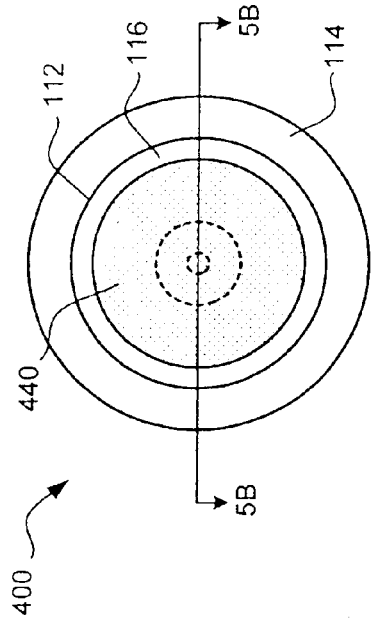
FIG. 4A is top view of a body portion of an endoscope seal utilizing a sealing material.

The following detailed description should be read with reference to the drawings in which similar elements and different drawings are numbered the same. The drawings, which are not necessarily to scale, depict illustrative embodiments and are not intended to limit the scope of the invention.

Refer now to FIG. 1A which illustrates a side view of an endoscope seal in accordance with the present invention. Endoscope seal 10 includes a main body portion 100, a plug portion 20 and an adapter ring portion 30. The details of main body portion 100 are discussed in more detail with reference to FIGS. 2A and 2B. Main body portions 200, 300, 400, and 500 as discussed in detail with reference FIGS. 3A-3B, FIGS. 4A-4B, FIGS. 5A-5B, and FIG. 6D, respectively, may be used in place of main body portion 100.

Main body portion 100 includes a body 112 having a proximal end and a distal end. An outwardly extending flange 114 is connected to the distal end of the body 112. An inwardly extending flange 116 is connected to the proximal end of the body 112. As best seen in FIG. 1B, a central lumen 120 extends through body 112, and a seal 140 is disposed in the lumen 120. Central lumen 120 is sized to accommodate the shaft of elongate device such as a biliary catheter (not shown).

The plug portion 20 is connected to the main body portion 100 by a flexible arm 22. The plug portion 20 includes a cap 24, a middle portion 26, and a flange 28. The flexible arm 22 allows the plug portion 20 to be inserted into the proximal end of the main body portion 100 and seal the central lumen 120 in the absence of any devices inserted therein.

The adapter ring portion 30 is connected to the main body portion 100 by a flexible arm 32. The adapter ring portion 30 includes an inwardly extending top flange 36 and an inwardly extending bottom flange 38 which together define a recess 37 within the ring 30. Adapter ring portion 30 also defines a central lumen 34. The flexible arm 32 permits the adapter ring portion 30 to be placed around the flange 114 of the main body portion 100. The adapter ring portion 30 permits the endoscope seal 10 to be connected to an endoscope having a larger diameter proximal end as will be discussed in more detail hereinafter.

Refer now to FIGS. 2A and 2B which illustrate the features of main body portion 100 in greater detail. Central lumen 120 includes a proximal port 121, an upper cavity 122, a middle cavity 124, a lower cavity 126, and a distal port 127. The proximal port 121 has an inside diameter slightly less than the outside diameter of the flange 28 of the plug portion 20. The upper cavity 122 is sized to accommodate the flange 28 of the plug portion 20. With this arrangement, the flange 28 may be snapped through the proximal port 121 into the upper cavity 122 such that the plug portion 20 effectively seals the central lumen 120 when no devices are present therein.

Distal port 127 is sized to be slightly smaller than the diameter of the proximal end of the endoscope. The lower cavity 126 is sized to accommodate the flange of the proximal end of the endoscope (not shown). Within the arrangement, the proximal end of the endoscope may be snapped into the distal port 127 to connect the endoscope seal 10 to the endoscope and to establish fluid communication between the central lumen 120 and the working channel of the endoscope.

If the proximal end of the endoscope is too large for the lower cavity 126 and distal port 127, the adapter ring portion 30 may be placed on the flange 114. Specifically, the lumen 34 of the adapter ring portion 30 has a diameter that is slightly less than the outside diameter of the flange 114. The recess 37 between the upper flange 36 and lower flange 38 of the adapter ring portion 30 is sized to accommodate the flange 114 leaving sufficient space to accommodate the proximal flange of the endoscope. With this arrangement, the adapter ring portion 30 may be snapped into place around the flange 114 and the proximal flange of the endoscope (not shown) may be snapped into the recess 37 of the adapter ring portion 30. Thus, the adapter ring portion 30 in combination with the flange 114 permits the endoscope seal 10 to fit endoscopes of different sizes.

With this arrangement, the distal end of the main body portion 100 may be connected to the proximal end of the endoscope (not shown). When the main body portion 100 is connected to the endoscope, the central lumen 120 is aligned with and in fluid communication with the working channel of the endoscope. The central lumen 120 is sized and adapted for insertion of an elongate device such as a biliary catheter. Thus, an elongate device may be inserted into the proximal end of the main body portion 100, through the lumen 120, and into the working channel of the endoscope.

The middle cavity 124 of the central lumen 120 is defined by the seal mechanism 140. Middle cavity 124 is conically shaped to facilitate easy insertion of an elongate device therein. The conically shaped cavity 124 tapers from a proximal aperture 142 to a distal aperture 144. A plurality of inwardly projecting protrusions 146 extend from the proximal aperture 142 to the distal aperture 144. Although eight protrusions 146 are illustrated, it is contemplated that virtually any member of protrusions 146 may be utilized. Protrusion 146 is uniformly spaced about the wall 148 defining the lumen 124. The protrusions 146 are sufficiently flexible to conform to a non-circular shaft of an elongate device inserted therein.

Figure 5A:
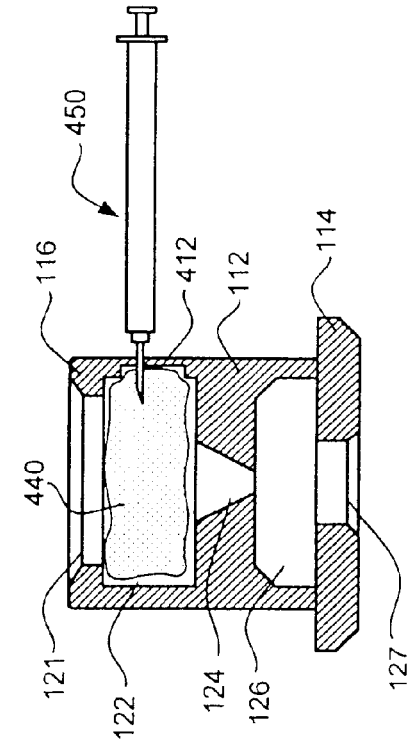
FIG. 5A is a top view of a body portion of an endoscope seal utilizing an injected sealing material.
Figure 6C:
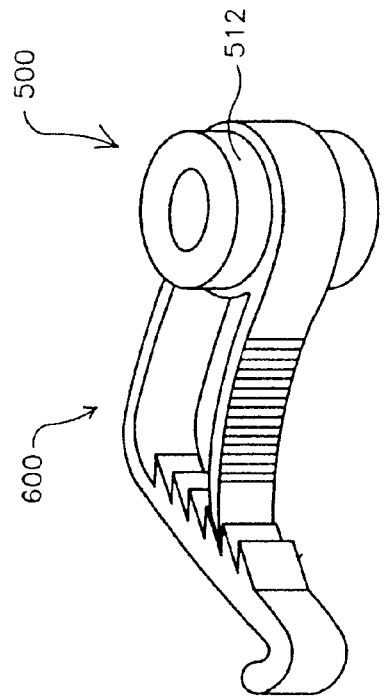
FIG. 6C is an isometric view of the tightening ratchet illustrated in FIG. 6A disposed about a variable diameter main body portion.
Figure 6D:
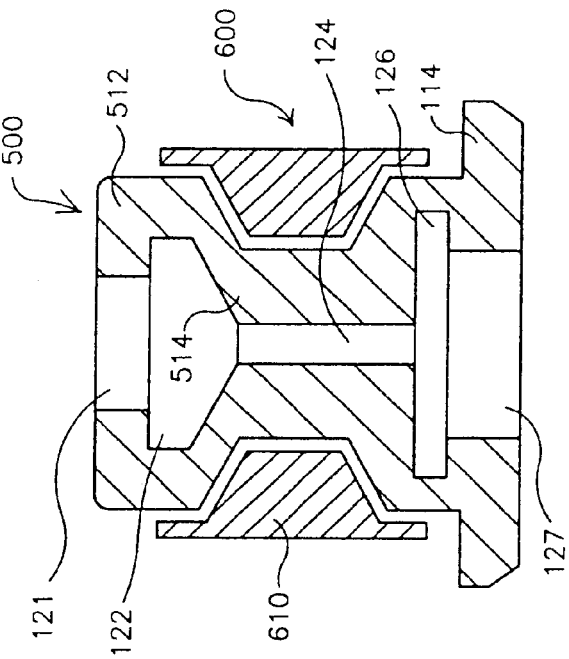
FIG. 6D is a cross-sectional view of the tightening ratchet disclosed about the variable diameter main body portion as illustrated in FIG. 6C.
Figure 6A:
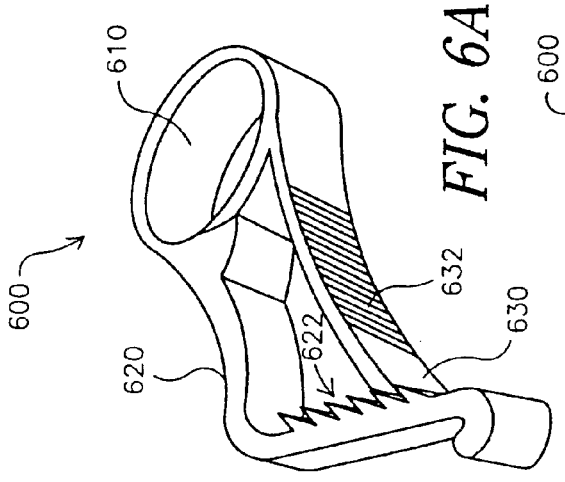
FIG. 6A is an isometric view of a tightening ratchet for use in combination with a variable diameter valve.
Figure 6B:
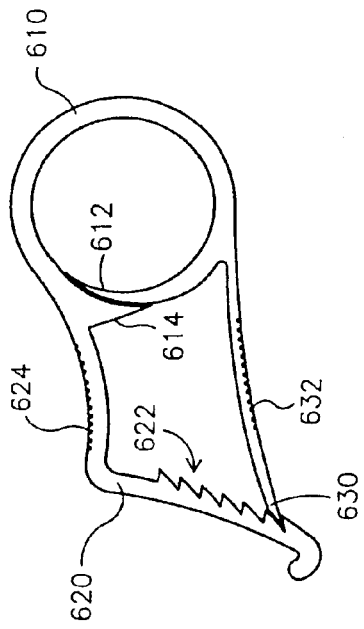
FIG. 6B is a top view of the tightening ratchet illustrated in FIG. 6A.

For example, if the non-circular shaft illustrated in FIGS. 5A and 6A of Agro et al. '971 was inserted into the seal mechanism 140, one or more of the protrusions 146 would be disposed in the non-circular portion (i.e., the C-shaped channel) of the shaft, thereby effectively sealing about the non-circular shaft. Although the protrusions 146 may not provide a fluid-tight seal about a non-circular shaft, it is believed that any decrease in the amount of fluid (bile and air) escaping from the working channel of the endoscope is a significant improvement. Accordingly, as used herein, the term seal may refer to a fluid-tight seal or a seal which significantly inhibits the egress of fluid. The entire endoscope seal 10 may be made of conventional materials using conventional techniques. For example, the endoscope seal 10 may be formed by injection molding a flexible medical grade silicone. From the functional description provided herein, those skilled in the art will readily appreciate that the endoscope seal 10 may be formed from a wide variety of suitable flexible materials such as rubber, silicon or elastomer. In addition, the endoscope seal 10 may be made by a variety of different manufacturing methods, but injection molding is preferred.

The endoscope seal 10 may have an overall length on the order of 3.670 inches. The flexible arms 22 and 32 may have a thickness on the order of 0.085 inches and a width on the order of 0.20 inches. The plug portion 20 may have a thickness of approximately 0.255 inches and an outside diameter of approximately 0.560 inches. The flange 28 of the plug 20 may have an outside diameter of approximately 0.400 inches and a thickness of approximately 0.085 inches. The middle portion 26 of the plug 20 may have a diameter of approximately 0.320 inches and a thickness of approximately 0.085 inches.

The adapter ring portion 30 may have an outside diameter portion of approximately 0.780 inches, an inside diameter of approximately 0.500 inches, and a thickness of approximately 0.260 inches. The top flange 36 and the bottom flange 38 of the adaptor ring portion 30 may have a thickness of approximately 0.065 inches, and the recess 37 may be approximately 0.040 inches deep.

The main body portion 100 may have an overall height of approximately 0.550 inches. The body 112 may have a diameter of approximately 0.560 inches and a height of approximately 0.480 inches. The flange 114 may have an outside diameter of approximately 0.680 inches and a thickness of approximately 0.70 inches. The proximal port 121 may have an inside diameter tapering from approximately 0.400 inches to an approximately 0.320 inches. Similarly, the distal port 127 may have an inside diameter tapering from approximately 0.280 inches to approximately 0.200 inches. The upper cavity 122 may have a diameter of 0.400 inches and a height of approximately 0.110 inches. The lower cavity 126 may have a diameter of approximately 0.350 inches and a height of approximately 0.130 inches. The middle cavity 124 may have an inside diameter tapering from approximately 0.170 inches to approximately 0.040 inches. The individual protrusions 146 may be tapered from the proximal aperture 142 to the distal aperture 144, having a width of approximately 0.020 inches tapering to approximately 0.015 inches. The protrusions 146 may be separated by slots, each having a width tapering from approximately 0.023 inches to approximately 0.003 inches.

Those skilled in the art will recognize that the endoscope seal 10 may have dimensions different than the above dimensions, which are provided for purposes of illustration only.

Refer now FIGS. 3A and 3B which illustrate body portion 200 in accordance with an alternative embodiment of the present invention. As mentioned previously, body portion 200 may be used in place of body portion 100 as described with reference to FIGS. 1A, 1B, 2A, and 2B. Except as described hereinafter and except as shown in the drawings, body portion 200 is the same in design and function as body portion 100.

Main body portion 200 includes a seal mechanism 240. Seal mechanism 240 includes a single protrusion 246 extending radially inward. Protrusion 246 extends from a proximal aperture 242 to a distal aperture 244. Protrusion 246 may have a wide variety of geometries, but preferably has a geometry that mates with the non-circular portion of the shaft of the elongate device inserted into the central lumen 120. For example, if the non-circular shaft illustrated in FIGS. 5A and 6A of Agro et al '971 were disposed in the central lumen 120, the single protrusion 246 would preferably have a geometry conforming to the slot of the C-shaped channel. Those skilled in the art will recognize that other non-circular shafts may be utilized and that the protrusion 246 may be modified to mate with the non-circular portion thereof.

Because the single protrusions 246 will limit rotation of the elongate device inserted through the central lumen 120, it may be desirable to permit rotation of the main body portion 200. This may be accomplished, for example, by providing a low-friction connection between the distal end of the main body portion 200 and the proximal end of the endoscope. A low-friction connection may be accomplished by a variety of means, such as by utilizing low-friction materials and lubricants.

Figure 4B:
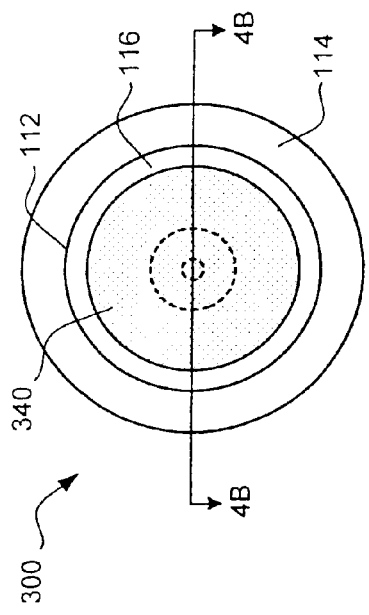
FIG. 4B is a cross-sectional view taken along line 4B-4B in FIG. 4A.

Refer now to FIGS. 4A and 4B which illustrate main body portion 300 in accordance with yet another embodiment of the present invention. As mentioned previously, main body portion 300 may be used in place of main boy portion 100 described with reference to FIGS. 1A, 1B, 2A, and 2B. Except as described hereinafter and except illustrated in the drawings, main body portion 300 is the same in design and function as main body portion 100. In this particular embodiment, main body portion 300 utilizes includes a seal 140 comprising a material having characteristics of easy penetration high-fluid absorption, and tear resistance, such as a surgical foam to seal about the non-circular shaft. Sealing material 340 is disposed in the upper cavity 122, and to accommodate the sealing material 340, the height of the upper cavity 122 is increased at the expense of the height of the middle cavity 124. Although not shown, a liquid drainage line and reservoir may be connected to the upper cavity 122 to drain excess fluid (bile and air) therefrom.

The sealing material 340 may comprise virtually any suitable medical grade material that has easy penetration, high-fluid absorption, and tear resistance characteristics. Preferably, the sealing material comprises a closed-cell medium density surgical foam commercially available from Rynel of Maine. When a non-circular shaft of an elongate device is inserted through the sealing material 340, the sealing material 340 tends to create a passage conforming to the profile of the non-circular shaft, thereby effective sealing about the non-circular shaft.

The sealing material 340 may be relatively liquid or relatively solid. For example, the sealing material 340 may be relatively solid such that it is suitable for molding into a wide variety of desired shapes. The sealing material 340 may be molded to fit in the upper cavity 122 and to have a pilot hole extending therethrough. Whether the sealing material 340 is in the form of a liquid or solid, the plug portion 20 may be utilized to keep the sealing material 340 contained in the upper cavity 122 prior to use.

The sealing material may alternatively comprise fibrous materials that are very compliant and fluid absorbent such as cotton or synthetic fabrics. Alternatively, the sealing material 340 may comprise a gel-like material to develop a very lubricious and compliant seal. The sealing material 340 may be cold-molded or insert-molded and a lubricant may be added to the sealing material to reduce friction and increase fluid absorption.

Figure 5B:
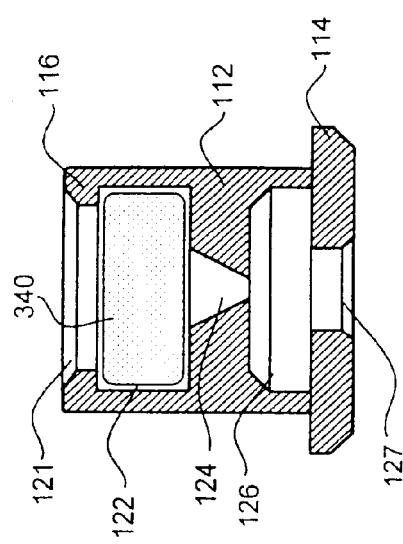
FIG. 5B is a cross-sectional view taken along line 5B-5B in FIG. 5A (FIG. 5B also illustrates an injection apparatus)

Refer now to FIGS. 5A and 5B, which illustrate main body portion 400 in accordance with yet another alternative embodiment of the present invention. Except as described hereinafter and except as illustrated in the drawings, main body portion 400 is the same in design and function as main body portion 300 described in reference to FIGS. 4A and 4B. Main body portion 400 includes an injectable sealing material 440 that may be injected into the upper cavity 122 just prior to use. To facilitate such injection, the body 112 may be provided with a thin-walled section 412. A suitable injection device such as a syringe 450 may be used to pierce the thin-walled portion 412 and inject the liquid sealing material 440. Sealing material 440 may be injected into the upper cavity 122 with the plug portion 20 inserted into the proximal end of the main body portion 400 to contain the sealing material 440 in the upper cavity 122 prior to use. Sealing material 440 has the same properties and performs the same function as sealing material 340 described with reference to FIGS. 4A and 4B, except sealing material 440 has a lower initial viscosity.

Refer now to FIGS. 6A, 6B, 6C, and 6D which illustrate a variable diameter main body portion 500 and tightening ratchet 600 for use therewith. Except as described herein and except as shown in the drawings, variable diameter body main portion 500 is the same in design and function as main body portion 100 described with reference to FIGS. 1A, 1B, 2A, and 2B. The body 512 includes a central waist portion 514 that facilitates compression of the lumen 124 at relatively low forces due to the reduced diameter of the waist 514. However, it is contemplated that the compressive forces of the tightening ratchet 600 may be used with or without the reduced diameter waist portion 514. In particular, the tightening ratchet 600 may be used with a constant diameter body 512. By actuating tightening ratchet 600 disposed about the variable diameter main body portion 500 as illustrated in FIGS. 6C and 6D, the central cavity 124 reduces in diameter and seals about the non-circular shaft of the elongate device extending therethrough.

Tightening ratchet 600 includes a hoop 610 that may vary in diameter by virtue of the sliding ends 612 and 614. Note that if a reduced diameter waist portion 514 is provided on the variable diameter main body portion 500, the hoop 610 may include a conforming geometry as illustrated in FIG. 6D. Tightening ratchet 600 further includes a plurality of teeth 622 that engage a lever arm 630 to lock the moving ends 612 and 614 of the hoop 610 as the diameter of the hoop 610 is decreased. The teeth 622 are disposed on a flexible arm 620 that is normally biased against the lever arm 630 but may be deflected to permit the teeth 622 to disengage the lever arm 630, thereby permitting the ends 612 and 614 of the loop 610 to move and thereby increase the diameter of the hoop 610. Both the flexible arm 620 and the lever arm 630 may include gripping surfaces 624 and 632, respectively, to facilitate easy gripping of the tightening ratchet 600. Those skilled in the art will recognize that there are many alternative compression mechanisms to tightening ratchet 600, such as a screw-type compression clamp, a spring compression clamp, etc.

Refer now to FIGS. 7A, 7B and 7C which illustrate main body portion 700 in accordance with another embodiment of the present invention. Except as described herein and except as illustrated in the drawings, main body portion 700 is the same in design and function as main body portion 200 described with reference to FIGS. 3A and 3B. Main body portion 700 includes a seal mechanism 740. Seal mechanism 740 includes a sealing mandrel 746 extending through the central lumen 120. Sealing mandrel 746 may have a wide variety of cross-sectional geometries, but preferably has a geometry that mates with the non-circular portion of the shaft of the elongate device inserted into the central lumen 120. For example, if the non-circular shaft illustrated in FIGS. 5A and 6A of Agro et al. '971 were disclosed in the central lumen 120, the sealing mandrel 746 would preferably have a geometry conforming to the slot of this C-shaped channel, as best seen in FIG. 7C. The entire length of the sealing mandrel 746 may have a conforming geometry or only the portion of the sealing mandrel 746 extending from the proximal aperture 742 to the distal aperture 744 may have a conforming geometry while the remainder of the sealing mandrel 746 has a different cross-sectional geometry, such as a circular cross-section. Those skilled in the art will recognize that other non-circular shafts may be utilized and that the sealing mandrel 746 may be modified to have a cross-sectional geometry that mates with the non-circular portion thereof. Thus, with the sealing mandrel 746 disposed in the slot of the biliary catheter (such as biliary catheter disclosed in Agro et al. '971), the collective cross-sectional profile is essentially circular such that the circular aperture 744 is able to establish a fluid tight seal.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A system for holding an elongate medical device relative to an endoscope comprising:
    an endoscope having an access port; and
    an endoscope seal main body portion releasably affixed to the access port, the endoscope seal main body portion having
        a body with a cavity,
        a sealing element disposed in the cavity, the sealing element having a passageway extending therethrough configured to sealingly receive the elongate medical device; and
        a waist with a reduced diameter;
    wherein the endoscope seal main body portion further includes
        a ratchet member disposed about the waist with reduced diameter of the main body portion for evenly applying compressive forces circumferentially on the main body portion, the sealing element, or both the main body portion and the sealing element, when the endoscope seal main body portion is releasably affixed to the access port; and wherein the access port of the endoscope has a flange and the endoscope seal main body portion releasably affixes to the access port by receiving the flange therein at a distal port that is positioned at a distal end of the endoscope seal main body portion.

2. The system of claim 1, wherein the sealing element is foam.

3. The system of claim 2, wherein the body is rubber.

4. The system of claim 1, wherein the sealing element is molded to fit the cavity, and the passageway is a pilot hole.

5. The system of claim 1, wherein the sealing element includes at least one protrusion extending into the passageway for sealingly receiving the elongate medical device.

6. The system of claim 1, wherein the elongate medical device is a catheter.

7. The system of claim 1, wherein the elongate medical device is a guidewire.

8. The system of claim 1, wherein at least a portion of the elongate medical device has a non-circular cross-sectional shape.

* * * * *